US012746001B1

(12) United States Patent
Hawasli

(10) Patent No.: US 12,746,001 B1
(45) Date of Patent: Sep. 29, 2026

(54) FASCIA SUTURING SYSTEM

(71) Applicant: Abdelkader Hawasli, Saint Clair Shores, MI (US)

(72) Inventor: Abdelkader Hawasli, Saint Clair Shores, MI (US)

( * ) Notice: Subject to any disclaimer, the term of this patent is extended or adjusted under 35 U.S.C. 154(b) by 330 days.

(21) Appl. No.: 18/431,266

(22) Filed: Feb. 2, 2024

(51) Int. Cl.
*A61B 17/04* (2006.01)

(52) U.S. Cl.
CPC ...... *A61B 17/0469* (2013.01); *A61B 17/0482* (2013.01)

(58) Field of Classification Search
CPC . A61B 17/0469; A61B 17/0482; A61B 17/04; A61B 17/0483; A61B 17/0485; A61B 17/0491; A61B 2017/00637; A61B 2017/0472; A61B 2017/047; A61B 2017/00663
See application file for complete search history.

(56) References Cited

U.S. PATENT DOCUMENTS

| | | | | |
|---|---|---|---|---|
| 9,451,950 | B2 | 9/2016 | Patel et al. | |
| 9,668,724 | B2 * | 6/2017 | Tang | A61B 17/0469 |
| 9,675,342 | B2 * | 6/2017 | Prior | A61B 17/0482 |
| 9,833,233 | B2 | 12/2017 | Hammerland et al. | |
| 10,299,774 | B2 * | 5/2019 | Heneveld | A61B 17/0485 |
| 10,307,144 | B2 * | 6/2019 | Wu | A61B 17/0482 |
| 10,327,761 | B2 * | 6/2019 | Ho | A61B 17/0057 |
| 12,484,894 | B2 * | 12/2025 | Bromley | A61B 17/0482 |
| 2008/0033459 | A1 | 2/2008 | Sahfi et al. | |
| 2013/0165956 | A1 * | 6/2013 | Sherts | A61B 17/0482 606/148 |
| 2014/0296881 | A1 | 10/2014 | Ranucci et al. | |
| 2014/0350576 | A1 | 11/2014 | Patel et al. | |
| 2015/0157316 | A1 * | 6/2015 | Labarbera | A61B 17/0491 606/144 |
| 2016/0095589 | A1 | 4/2016 | Sherwinter | |

FOREIGN PATENT DOCUMENTS

| | | | |
|---|---|---|---|
| EP | 3612105 | A1 | 10/2018 |

OTHER PUBLICATIONS

The Weck® EFx Shield® Fascial Closure System. Product Description [online]. © 2024 Teleflex Incorporated. [retrieved on]. Retrieved from the Internet: <URL: https://www.teleflex.com/usa/en/product-areas/surgical/fascial-closure/weck-efx-shield-fascial-closure-system/>.

* cited by examiner

*Primary Examiner* — Dianne Dornbusch
(74) *Attorney, Agent, or Firm* — Cramer Patent & Design, PLLC.; Aaron R. Cramer

(57) ABSTRACT

The fascia suturing system may comprise a suture delivery device and a suture retriever. The fascia suturing system may assist in closing a laparoscopic incision. The suture delivery device may be adapted to be inserted into the laparoscopic incision and reconfigured to deploy a plurality of wings and a plurality of shields. The suture delivery device may position two sutures beneath subcutaneous layers of skin. The suture retriever may repeatedly penetrate the skin guided by the suture delivery device to grasp four ends of the two sutures which may each be retrieved as the suture retriever is withdrawn. The plurality of shields may prevent the suture retriever from piercing internal organs. The two sutures may be parallel to each other or may cross over. The fascia suturing system may be used to place a single suture by not affixing both sutures to the suture delivery device.

3 Claims, 13 Drawing Sheets

FASCIA SUTURING SYSTEM

RELATED APPLICATIONS

This application claims the benefit of priority to U.S. Provisional Application No. 63/577,561, filed Apr. 28, 2023, which is incorporated by reference herein in its entirety.

FIELD OF THE DEVICE

The present device pertains to the field of medical devices, specifically to surgical instruments designed for fascia suturing. It is particularly relevant to the domain of minimally invasive surgery, including laparoscopic and robotic surgical procedures.

BACKGROUND OF THE DEVICE

The present device represents a notable advancement in the field of minimally invasive surgery, particularly in the area of fascia suturing. This fascia suturing system, as detailed below, offers substantial improvements over traditional methods employed for fascia closure following laparoscopic or robotic surgeries.

Traditional fascia closure techniques typically involve manual suturing. This conventional approach, while effective, is often time-consuming and demands a high degree of skill from the surgeon. Furthermore, it carries inherent risks associated with inconsistent suture placement, potentially leading to complications such as incisional hernias. Manual suturing also extends the duration of the surgery, thereby increasing the patient's exposure to anesthesia, which in turn can elevate the risk of related complications.

In contrast, the development of this fascia suturing system addresses these challenges by simplifying the suturing process. It allows for precise and reliable closure of fascia openings, significantly reducing the risk of postoperative complications. One of the key features of this system is its ability to place multiple sutures simultaneously. This functionality not only enhances the security of the closure but also contributes to a reduction in operative time. By minimizing the duration of the surgery, the system effectively reduces the patient's exposure to anesthesia, diminishing the associated risks.

The present device comprises at least one enhancement to the WECK® EFX Shield® Fascial Closure System. The WECK® EFX Shield® Fascial Closure System may be covered by one or more of the following patents: U.S. Pat. Nos. 9,492,163; 9,539,002; 10,251,640; 10,470,750; AU 2014364039; AU 2014364043; CA 2932469; CA 2933197; CN 105828729; CN 105848591; CN 109009255; EP 3079600; JP 6246935; JP 6353051; KR 10-1904628; KR 10-1919211. The enhancements included in the present device represent non-obvious improvements upon the prior art, and aim to further streamline the fascia suturing process and augment the overall efficiency and safety of minimally invasive surgical procedures.

SUMMARY OF THE DEVICE

This disclosure describes various embodiments of a fascia suturing system, designed for minimally invasive surgical procedures. Central to these embodiments is a suture delivery device, featuring a delivery body configured for insertion through a laparoscopic or robotic skin incision into a patient's abdominal cavity. In certain embodiments, this device is equipped with a plurality of deployable wings and shields, facilitating the positioning of at least two sutures beneath a fascia opening and a peritoneum layer. Each of these sutures possesses first and second free ends.

Several embodiments include a suture retriever, designed to work in tandem with the suture delivery device to achieve fascia closure. This retriever may comprise an ergonomically designed handle, enhancing user comfort and control. Integrated into the handle is a push button, used to actuate a pair of pinchers within the needle of the suture retriever. This mechanism is specifically crafted to securely grasp and retrieve individual sutures.

In certain embodiments, the suture delivery device is equipped with a stopper, located on the delivery body. This stopper is specifically designed to limit the depth of insertion into the laparoscopic or robotic skin incision. Additionally, the stopper may feature a pair of notches on each side, purposed for holding the first and second suture free ends during insertion.

The delivery body of the suture delivery device is thoughtfully divided into three distinct portions in some embodiments: a proximal portion, a middle portion, and a distal portion. The proximal portion extends from the proximal end to the stopper, while the middle portion spans from the stopper to a pivot junction for the deployable wings. The distal portion, extending from this pivot junction to the distal end of the delivery body, is designed for insertion into the abdominal cavity through the fascia opening and peritoneum layer, particularly during the closing procedure.

Furthermore, some embodiments feature a wing plane in the suture delivery device. This is an imaginary plane that bisects the device longitudinally, passing through its central axis and the center of the deployable wings, effectively dividing the device into a front half and a rear half.

The suture delivery device in certain embodiments includes an actuator rod and a pull rod mechanism. This setup is integral for the deployment and retraction of the deployable wings and shields. The actuator rod and pull rod mechanism facilitate longitudinal movement within an actuator lumen of the delivery body. Additionally, the delivery body is equipped with a series of needle guide lumens, strategically positioned to guide the needle of the suture retriever during the suture retrieval process.

Some embodiments also position at least two of these needle guide lumens in front of the wing plane and another two behind it. Moreover, the deployment of the deployable wings and shields is designed to form individual right triangle structures against the peritoneum layer of the inner abdominal wall. Each of these triangle structures comprises an individual wing and shield, forming the first leg and the hypotenuse, respectively.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY

Figure 1:
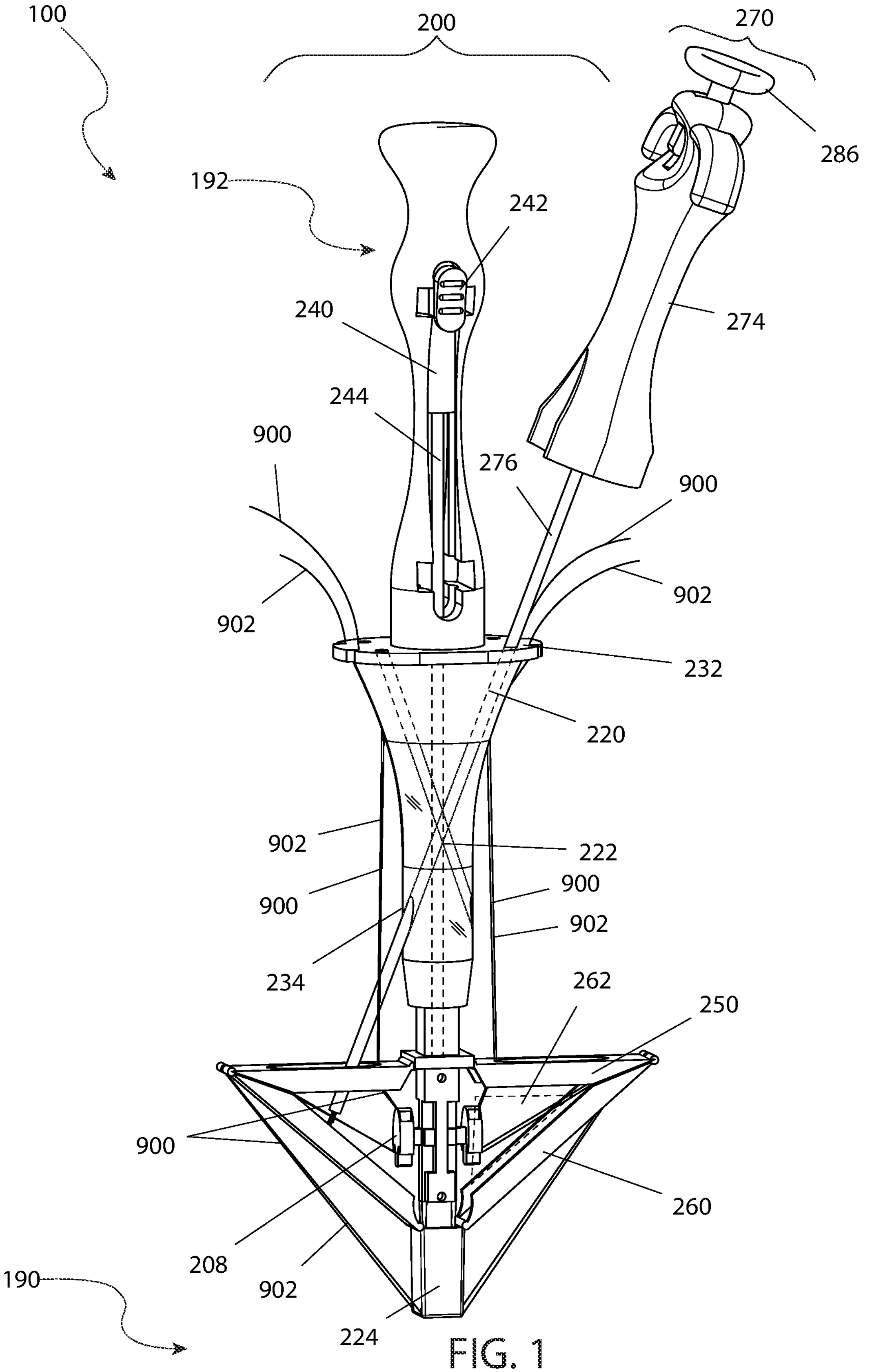
FIG. 1 is an isometric view of a fascia suturing system 100, according to an embodiment of the present invention, illustrating the suture delivery device 200 and the suture retriever 270.
Figure 7:
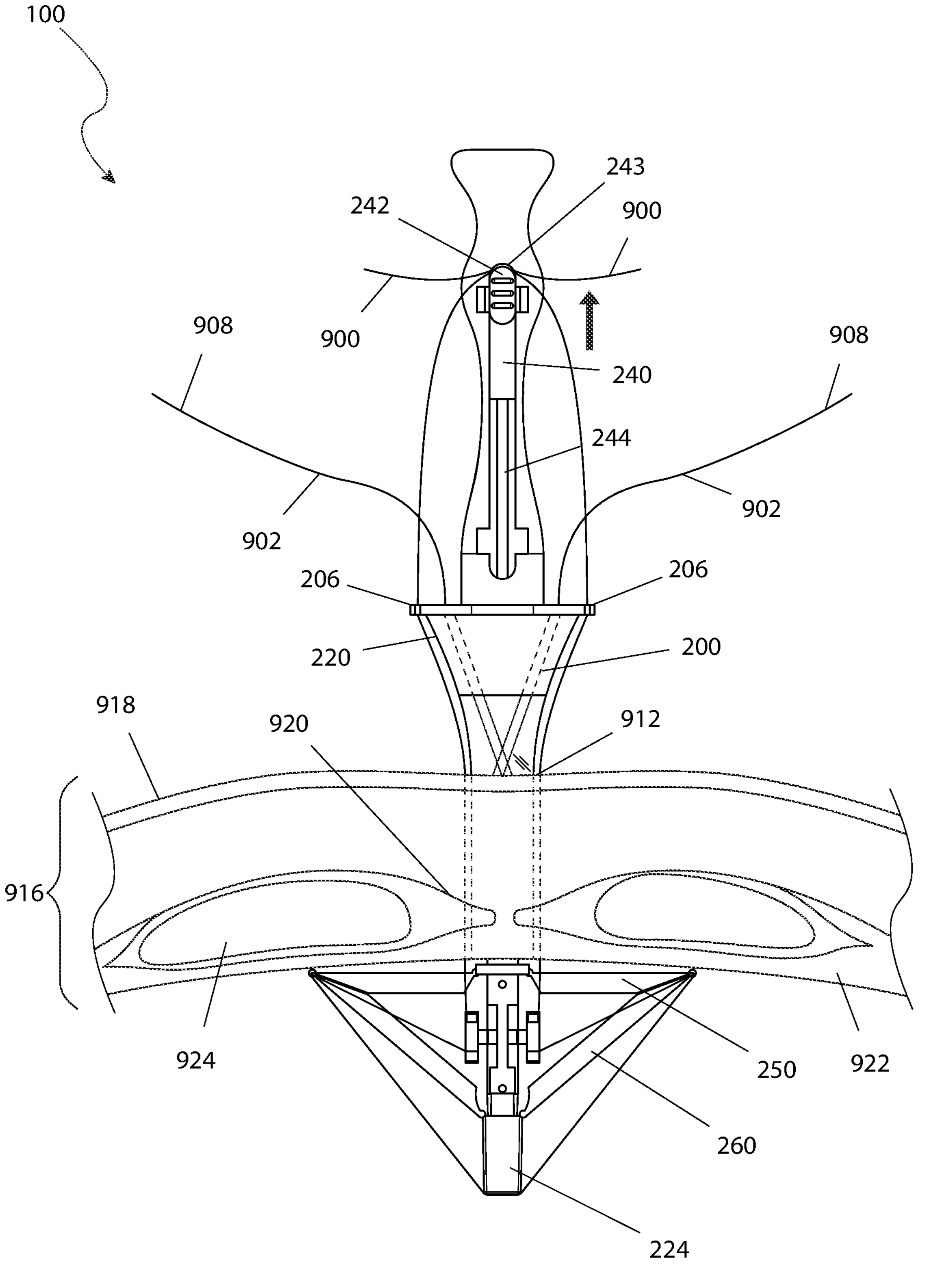
FIG. 7 is an in-use view of a fascia suturing system 100, according to an embodiment of the present invention, illustrating the suture delivery device 200 inserted into a laparoscopic incision 912 and with the plurality of wings 250 and the plurality of shields 260 deployed, also illustrating the first and second sutures 900, 902 in their mounted position on the stopper notch 206 with the first suture 900 being anchored on the pull rod handle groove 243.
Figure 8:
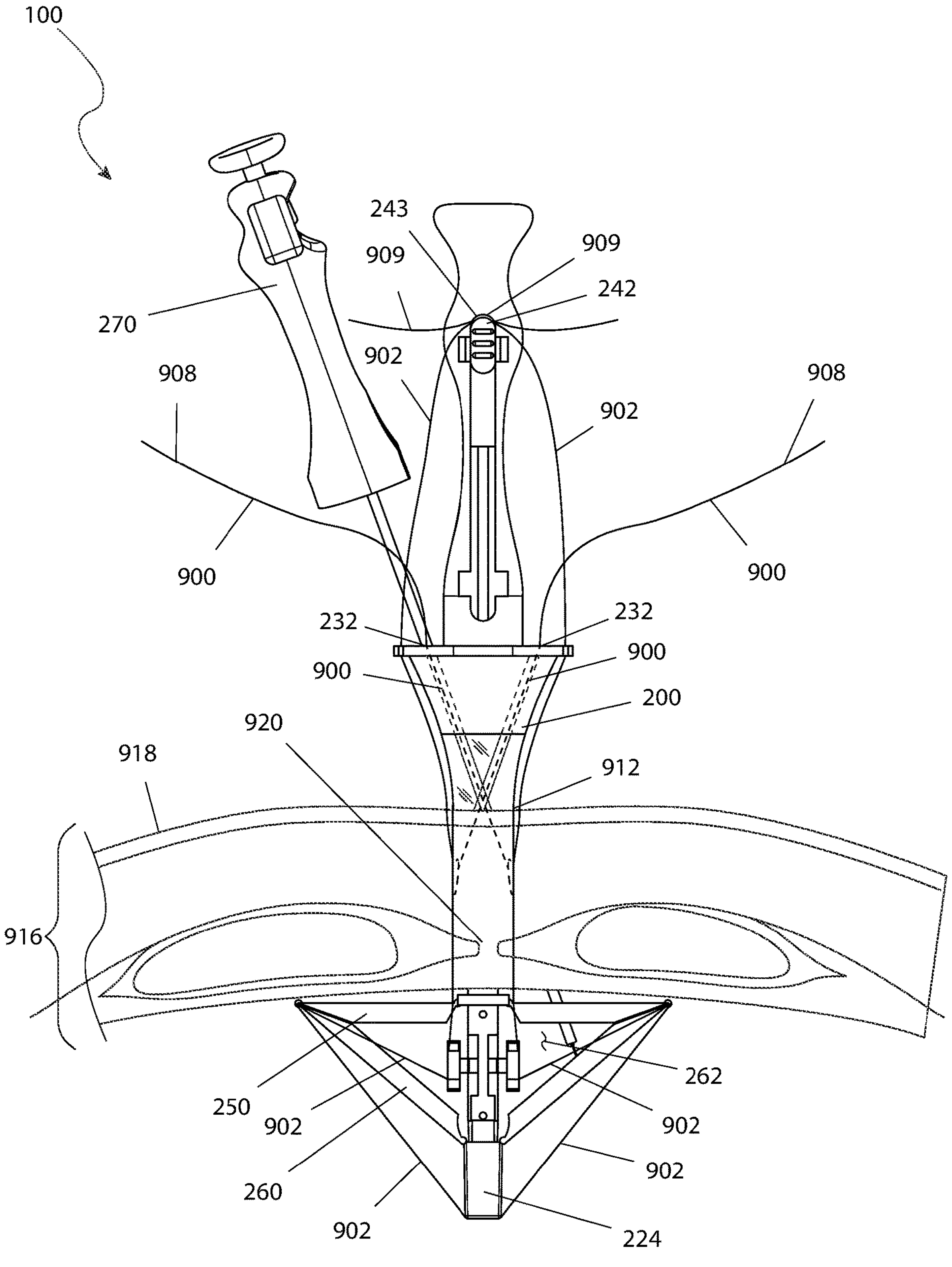
FIG. 8 is an in-use view of a fascia suturing system 100, according to an embodiment of the present invention, illustrating both first suture free ends 908 being pulled out through the needle guide opening 232 while the suture retriever is inserted through the suture deliver device 200 and grasping the second suture 902 from the suture retrieval space 262 while the second suture free ends 909 remain anchored on the pull rod handle groove 243.

100 fascia suturing system
190 proximal end
192 distal end
194 central longitudinal axis
200 suture delivery device
202 delivery body
204 suture positioning groove
206 stopper notch
208 suture guide
210 proximal portion
212 distal portion
214 middle portion
216 straight-across slot
218 crossing slot
220 stopper
222 actuator lumen
224 mounting structure
225 mounting structure groove
226 slot
228 suture guide notch 230 needle guide lumen
232 needle guide opening
234 needle guide exit
240 pull rod
242 pull rod handle
243 pull rod handle groove
244 actuator rod
250 wing
252 wing aperture
254 pull rod aperture
256 locking notch
260 shield
262 suture retrieval space
264 suture gap
270 suture retriever
274 retriever handle
276 needle
278 retriever spring
280 pincher
282 straight armature
284 hooked armature
286 push button
288 automatic stopper
290 locking window
292 finger hold
294 retriever lumen
900 first suture
902 second suture
908 first suture free end
909 second suture free end
912 laparoscopic or robotic skin incision
916 subcutaneous layers
918 outlying skin
920 fascia opening
922 peritoneum layer
924 muscle The present device is directed to a fascia suturing system (herein described as the "device") 100 as seen in FIG. 1. The fascia suturing system 100 may comprise a suture delivery device 200 and a suture retriever 270. The fascia suturing system 100 may assist in closing a laparoscopic or robotic fascia opening 920 as seen in FIG. 7. The suture delivery device 200 may be adapted to be inserted into a patient via the laparoscopic or robotic skin incision 912 and reconfigured to deploy a plurality of wings 250 and a plurality of shields 260 as seen in FIG. 7. The suture delivery device 200 will position two (2) sutures 900, 902 beneath the fascia opening 920 and peritoneum layer 922. The suture retriever 270 will repeatedly penetrate the muscle 924, fascia opening 920, and peritoneum layer 922 as guided by the suture delivery device 200 to grasp the first suture free end 908 and second suture free end 909 which may each be retrieved as the suture retriever 270 is withdrawn. The plurality of shields 260 prevent the suture retriever 270 from piercing any internal organs as seen in FIG. 8. The two (2) sutures 900, 902 may be parallel to each other or may cross over. Notwithstanding the ability of the fascia suturing system 100 to place two (2) sutures 900, 902, the fascia suturing system 100 may be used to place a single suture 900, 902 by not affixing both sutures 900, 902 to the suture delivery device 200.

Figure 2:
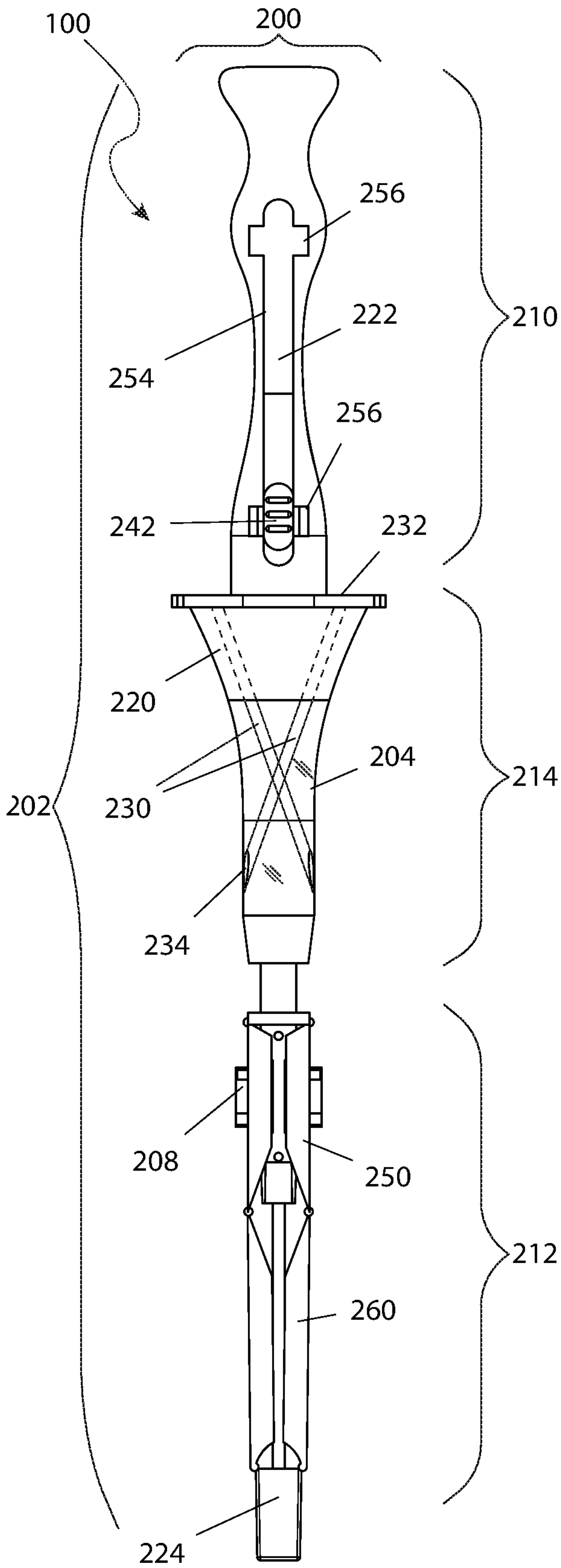
FIG. 2 is a side view of a fascia suturing system 100, according to an embodiment of the present invention, illustrating the suture delivery device 200.
Figure 3:
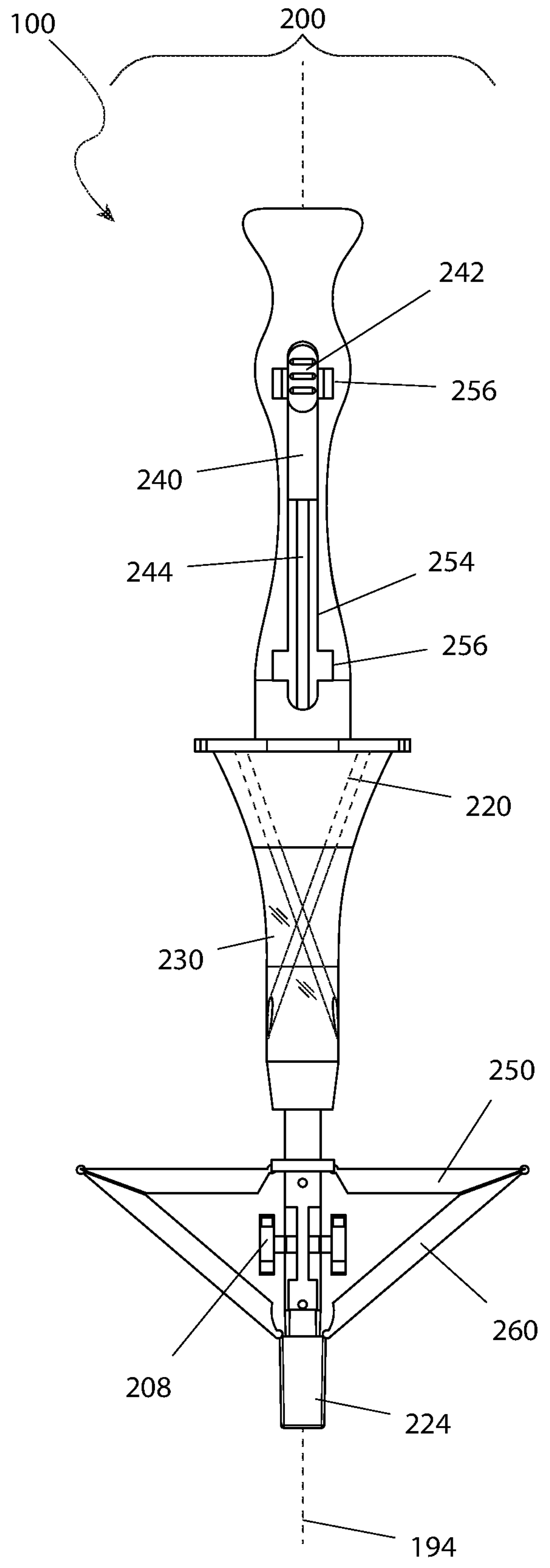
FIG. 3 is a front view of a fascia suturing system 100, according to an embodiment of the present invention, illustrating the suture delivery device 200 with the plurality of wings 250 and the plurality of shields 260 deployed.

The suture delivery device 200 may comprise a delivery body 202 as seen in FIG. 2 with an actuator lumen 222, an actuator rod 244, the plurality of wings 250 and the plurality of shields 260 as seen in FIG. 3. The two (2) sutures 900, 902 may be affixed to the suture delivery device 200 prior to inserting the suture delivery device 200 into the laparoscopic or robotic incision 912. Once inside the abdomen through the fascia opening 920 and peritoneum layer 922, the actuator rod 244 may be actuated to deploy the plurality of wings 250 and the plurality of shields 260 against the inner abdominal wall peritoneum layer 922 as seen in FIGS. 3 and 7.

The delivery body 202 may comprise a proximal portion 210, a middle portion 214, and a distal portion 212. The proximal portion 210 may extend from the proximal end 190 of the delivery body 202 to a stopper 220 as seen in FIG. 2. The middle portion 214 may extend from the stopper 220 to the pivot junction of the plurality of wings 250 and the delivery body 202. The distal portion 212 may extend from the pivot junction of the plurality of wings 250 and the delivery body 202 to the proximal end 190 of the delivery body 202. The middle portion 214 and the distal portion 212 may be inserted through the laparoscopic robotic skin incision 912 until the entire distal portion 212 is inside the abdominal cavity through the fascia opening 920 and the peritoneum layer 922 during a closing procedure while the middle portion 214 is located inside the subcutaneous layers 916 and the proximal portion 210 remains outside of the laparoscopic or robotic skin incision 912 as seen in FIG. 7. The proximal portion 210 may be adapted for a medical professional to grasp while operating the suture delivery device 200.

The delivery body 202 may define a wing plane. The wing plane may be an imaginary plane that passes through a central longitudinal axis 194 of the suture delivery device 200 and through the center of the plurality of wings 250. The wing plane effectively divides the suture delivery device 200 into a front half and a rear half. The wing plane may be useful in describing the structure and operation of the suture delivery device 200 as seen in FIG. 3.

Because of the orientation that the suture delivery device 200 is typically held during the closing procedure, the distal end 192 may be referred to as "top" or "up" and the proximal end 190 may be referred to as "bottom" or "down" as seen in FIG. 1.

The stopper 220 may be a funnel-shaped widening of the delivery body 202 as seen in FIG. 3. The stopper 220 may be operable to limit the insertion distance of the suture delivery device 200 into the laparoscopic or robotic skin incision 912. Specifically, the delivery body 202 of the suture delivery device 200 may be inserted into the laparoscopic or robotic skin incision 912 to the point where the stopper 220 contacts outlying skin 918 as seen in FIG. 7. In some embodiments, the distance between the stopper 220 and the plurality of wings 250 may be nine centimeters (9 cm) which may establish an appropriate depth for the suture delivery device 200 for obese patients during bariatric surgery. The stopper 220 may comprise a pair of stopper notches 206 on each side of the stopper 220 to hold the first suture free end 908 and second suture free end 909 while the suture delivery device 200 is inserted into the laparoscopic or robotic skin incision 912 as seen in FIG. 13.

Figure 4:
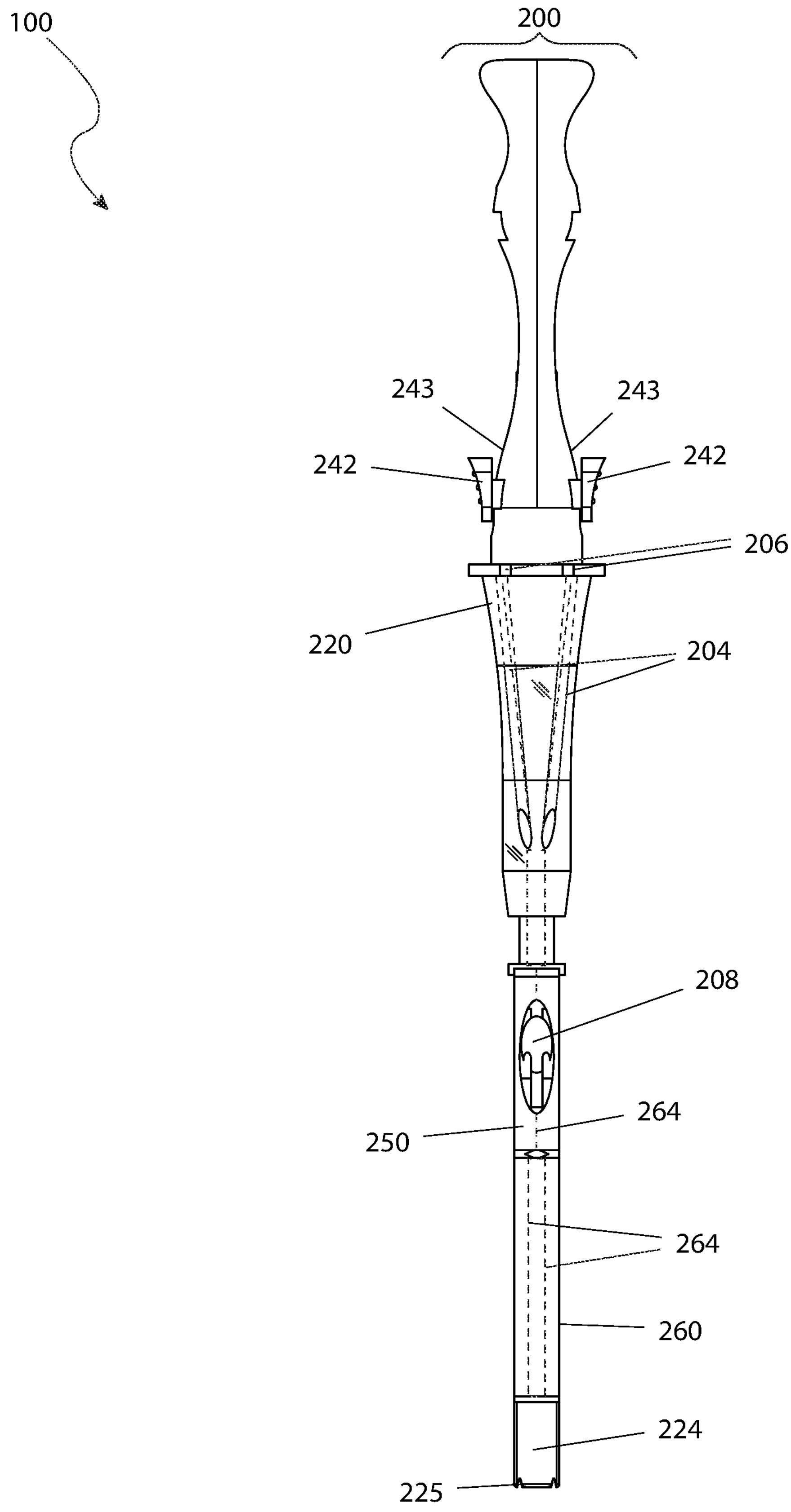
FIG. 4 is a side view of a fascia suturing system 100, according to an embodiment of the present invention, illustrating the suture delivery device 200 with the plurality of wings 250 and the plurality of shields 260 retracted.
Figure 5:
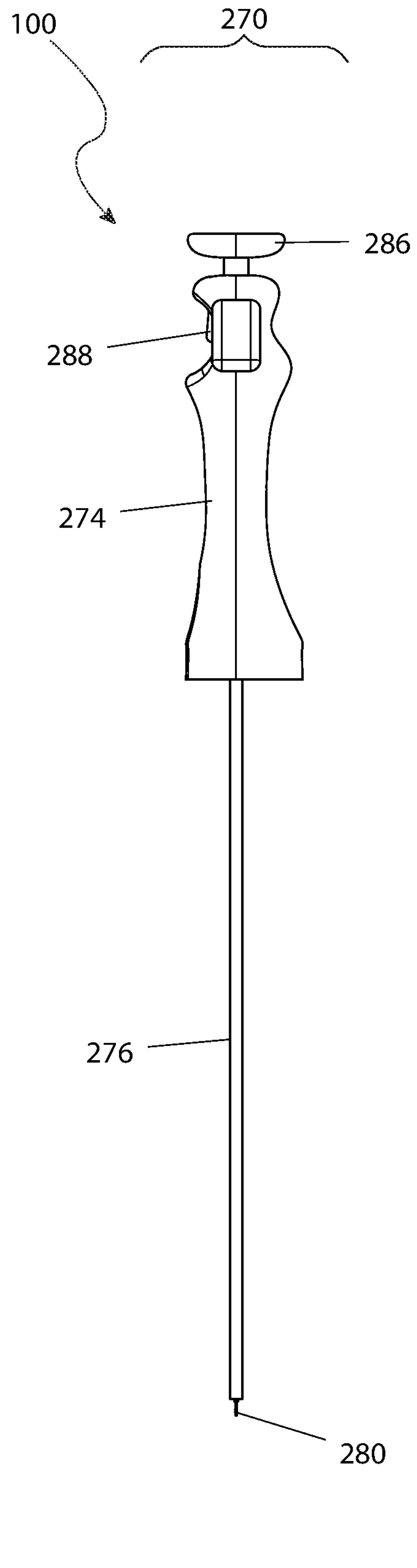
FIG. 5 is a side view of a fascia suturing system 100, according to an embodiment of the present invention, illustrating the suture retriever 270 with the pinchers 280 extended.
Figure 6:
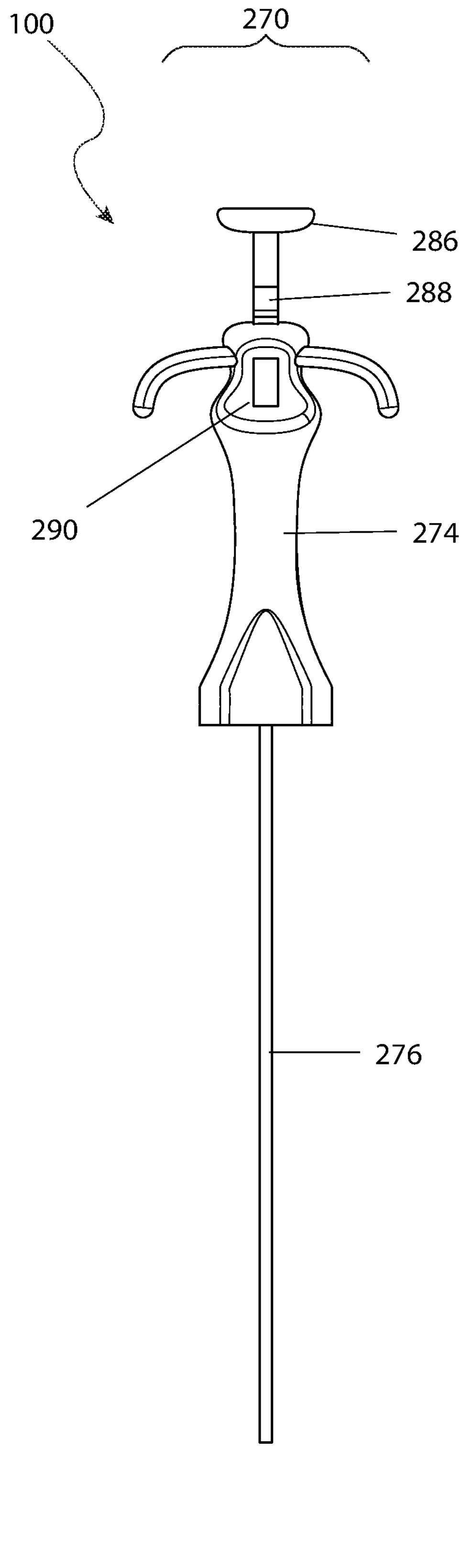
FIG. 6 is a front view of a fascia suturing system 100, according to an embodiment of the present invention, illustrating the suture retriever 270 with the pinchers 280 retracted.
Figure 11:
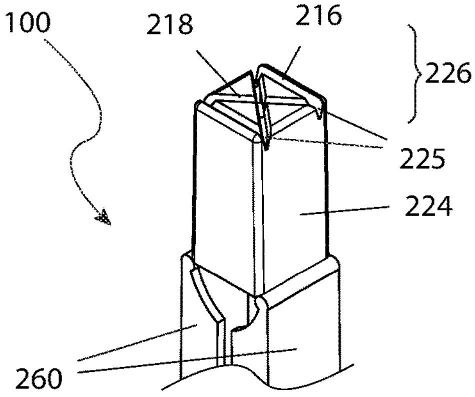
FIG. 11 is a detail view of a fascia suturing system 100, according to an embodiment of the present invention, illustrating pair of straight-across slots 216 and the pair of crossing slots 218 on the distal end of the mounting structure 224.
Figure 12:
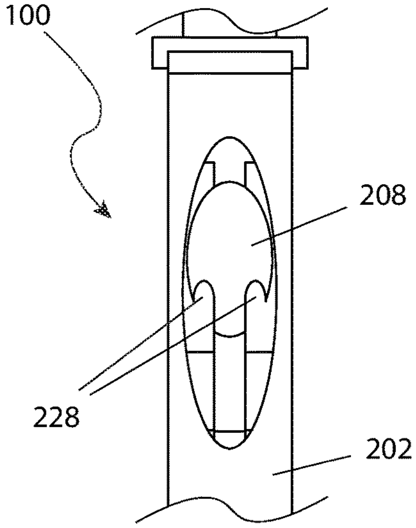
FIG. 12 is a detail view of a fascia suturing system 100, according to an embodiment of the present invention, illustrating a pair of suture guide notches 228 on a suture guide 208.
Figure 15:
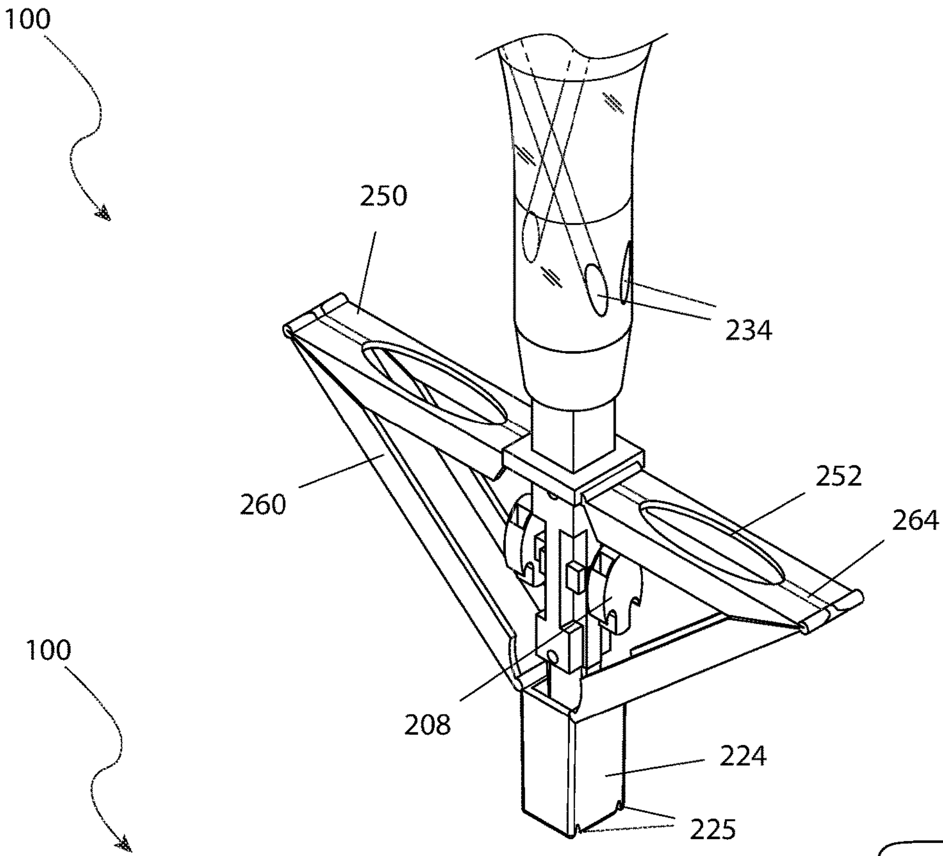
FIG. 15 is a detail view of a fascia suturing system 100, according to an embodiment of the present invention, illustrating the position of a suture guide 208.
Figure 16A:
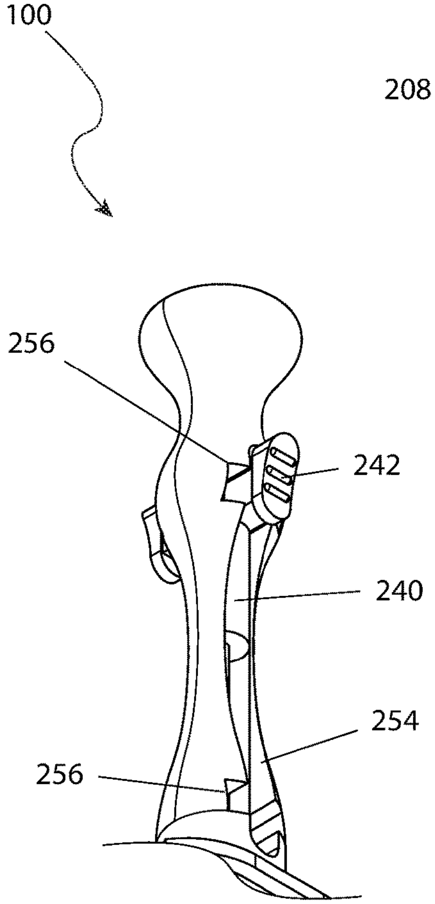
FIG. 16*a* is an isometric detail view of a fascia suturing system 100, according to an embodiment of the present invention, illustrating one (1) of the pair of pull rod apertures 254, one (1) of the pair of pull rod handles 242, and the pair of locking notches 256.
Figure 16B:
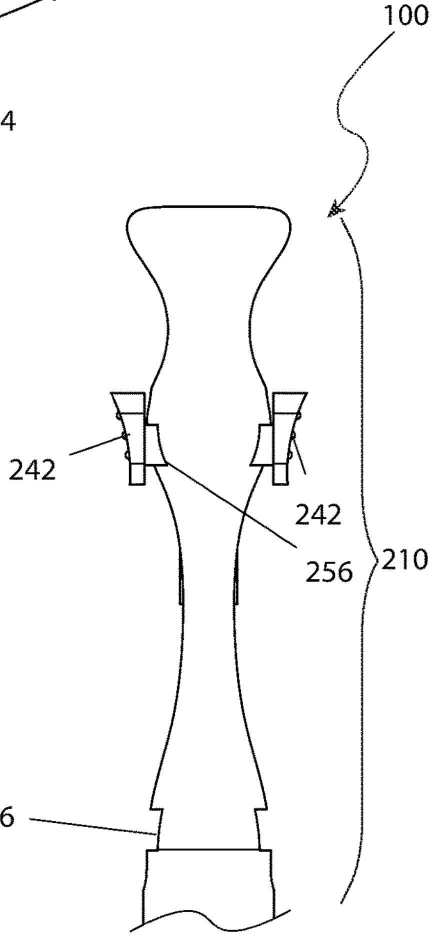
FIG. 16*b* is a side detail view of a fascia suturing system 100, according to an embodiment of the present invention, illustrating the pair of pull rod handles 242 and the pair of locking notches 256.

The delivery body 202 may comprise a suture guide 208 on each side of the delivery body 202 as seen in FIGS. 3, 4, 12, and 15. Each of the suture guides 208 may comprise a pair of suture guide notches 228 as seen in FIG. 12 located on the bottom of the suture guides 208 such that the suture guides 208 may retain the two (2) sutures against opposing sides of the delivery body 202 during deployment of the plurality of wings 250 as seen in FIG. 15 and the plurality of shields 260. The suture guides 208 may be positioned behind the plurality of wings 250 when the plurality of wings 250 are folded flat against the delivery body 202 and the suture guides 208 may be accessible via a wing aperture 252 as seen in FIG. 15 located on each of the plurality of wings 250. The middle portion 214 of the delivery body 202 may further comprise a pair of suture positioning grooves 204 as seen in FIGS. 2 and 4 running longitudinally along the sides of the delivery body 202 from the stopper 220 to the suture guides 208 and running on the outer surface of the plurality of shields 260. The pair of suture positioning grooves 204 may guide and retain the two (2) sutures 900, 902. The proximal end 190 of the suture delivery device 200 may comprise a mounting structure 224 as seen in FIGS. 1 and 11. The mounting structure 224 may comprise a pivot point for the bottom of the plurality of shields 260. The mounting structure 224 may comprise a plurality of slots 226 to guide the two (2) sutures 900, 902 around the bottom of the suture delivery device 200. The plurality of slots 226 may comprise a pair of straight-across slots 216 which may align the two (2) sutures 900, 902 to remain parallel and a pair of crossing slots 218 which may align the two (2) sutures 900, 902 to cross each other if a cross-suturing is desired.

Figure 13:
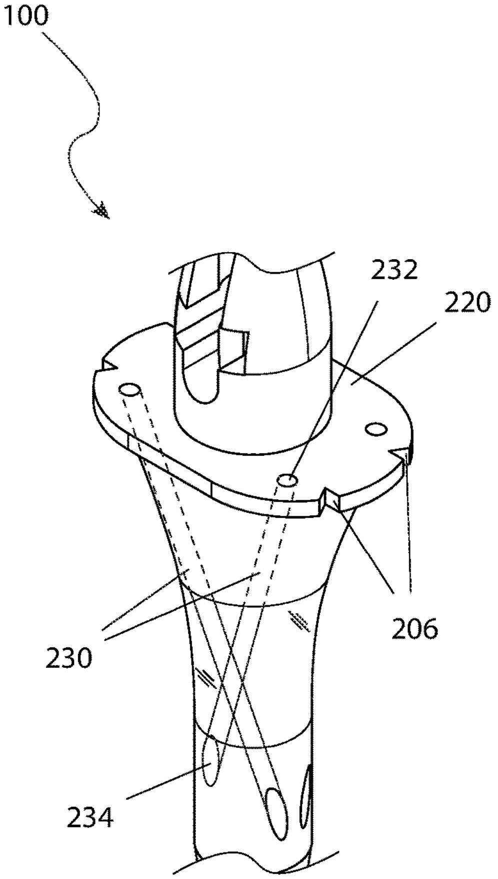
FIG. 13 is a detail view of a fascia suturing system 100, according to an embodiment of the present invention, illustrating a plurality of needle guide lumens 230.

The pair of stopper notches 206 as seen in FIG. 13, the pair of suture positioning grooves 204 as seen in FIG. 4, the suture guides 208 as seen in FIG. 4, and the plurality of slots 226 as seen in FIG. 11 on the mounting structure 224 may be aligned longitudinally on each side of the suture delivery device 200 such that each of the two (2) sutures 900, 902 may follow a path around the proximal end 190 of the suture delivery device 200 from one (1) side of the stopper 220 to the opposite side of the stopper 220.

Figure 18A:
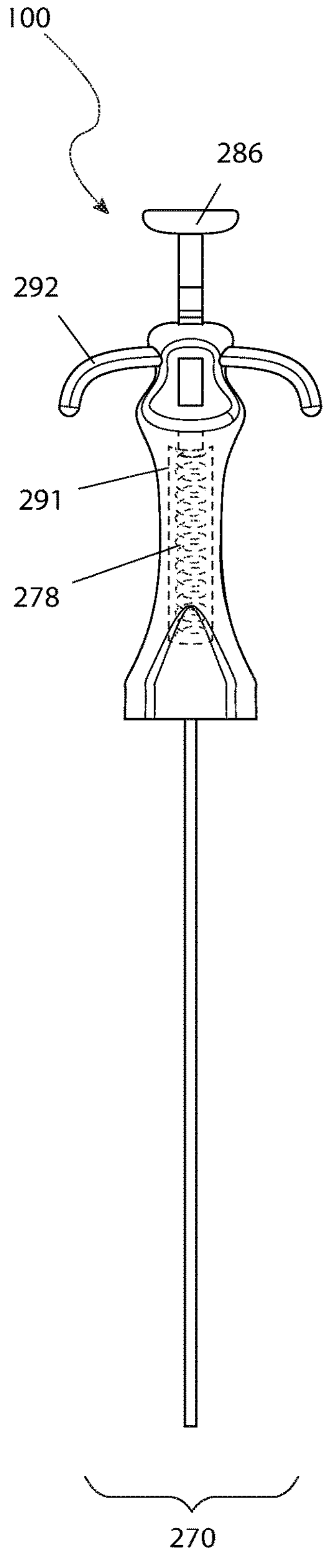
FIG. 18*a* is a detail view of a fascia suturing system 100, according to an embodiment of the present invention, illustrating the suture retriever.
Figure 18B:
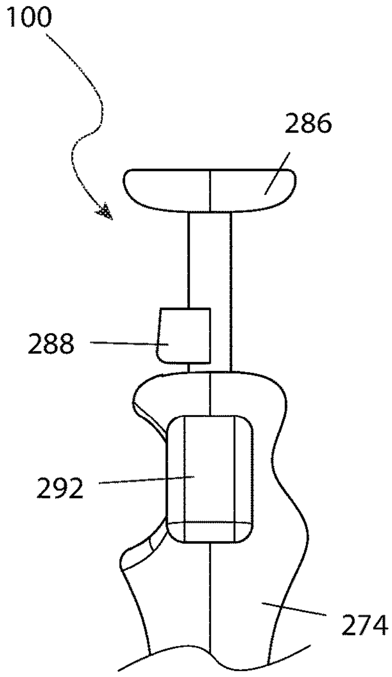
FIG. 18*b* is a side detail view of a fascia suturing system 100, according to an embodiment of the present invention, illustrating the push button 286 and automatic stopper 288 when the pair of pinchers are not deployed.
Figure 18C:
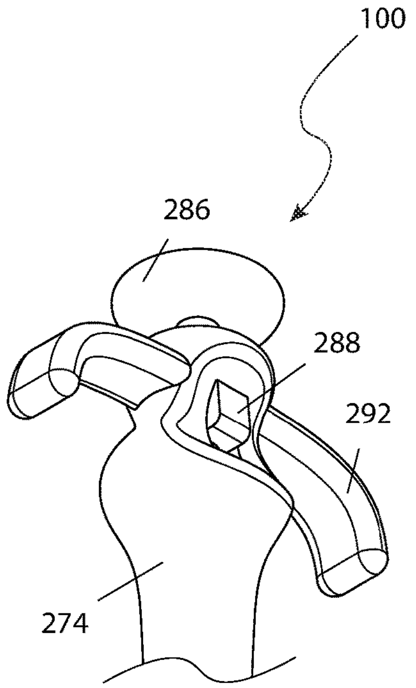
FIG. 18*c* is an isometric detail view of a fascia suturing system 100, according to an embodiment of the present invention, illustrating the push button 286 and automatic stopper 288 when the pair of pinchers are deployed.
Figure 18D:
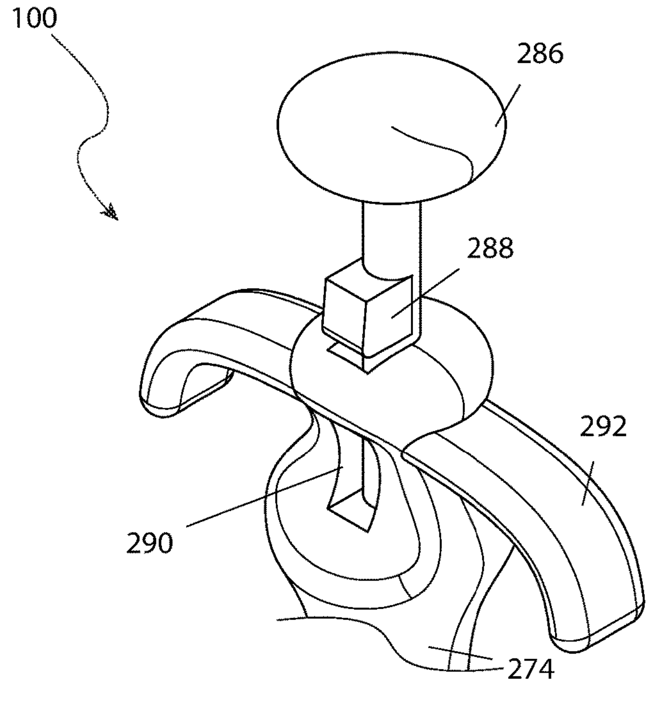
FIG. 18*d* is an isometric detail view of a fascia suturing system 100, according to an embodiment of the present invention, illustrating the push button 286, automatic stopper 288, and locking window 290 when the pair of pinchers are not deployed; and, FIG. 19 is a detail view of a fascia suturing system 100, according to an embodiment of the present invention, illustrating the straight armature 282 and the hooked armature 284 of the pair of pinchers 280.
Figure 19:
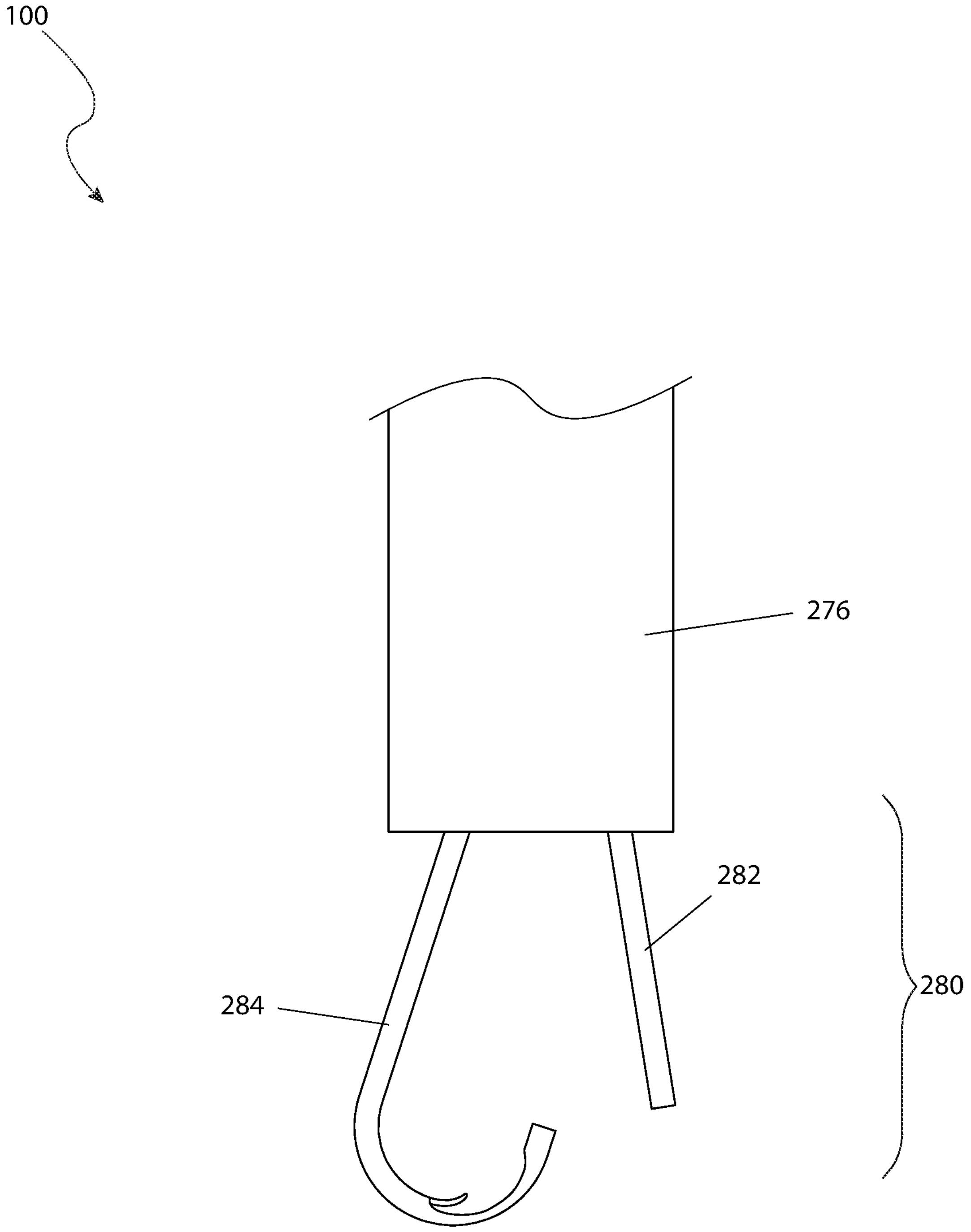

The delivery body 202 may comprise a plurality of needle guide lumens 230 as seen in FIGS. 2 and 3. The plurality of needle guide lumens 230 may guide a needle 276 as seen in FIG. 19 of the suture retriever 270 during the process of retrieving an end of an individual suture 900, 902 as seen in FIG. 18*a*. Two (2) of the plurality of needle guide lumens 230 may be located in front of the wing plane and two (2) of the plurality of needle guide lumens 230 may be located in behind the wing plane as seen in FIGS. 2 and 3. The portion of the of the plurality of needle guide lumens 230 is very close to the surface in the middle portion 214 to enable grasping of the separated two (2) sutures 900, 902. The front needle guide lumens 230 may be oriented at opposing oblique angles with respect to the central longitudinal axis 194 as seen in FIG. 3 of the suture delivery device 200. The rear needle guide lumens 230 may be mirror images of the front needle guide lumens 230.

Figure 17A:
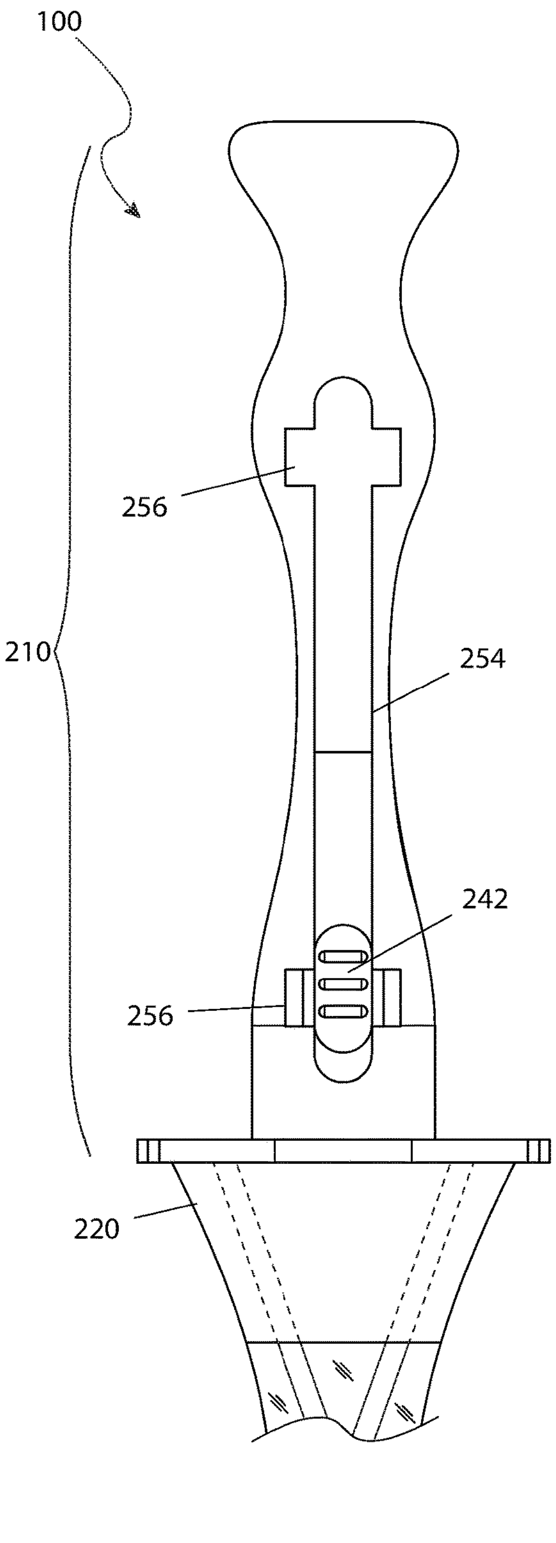
FIG. 17*a* is a front detail view of a fascia suturing system 100, according to an embodiment of the present invention, illustrating the proximal end 210 of the suture delivery device.
Figure 17B:
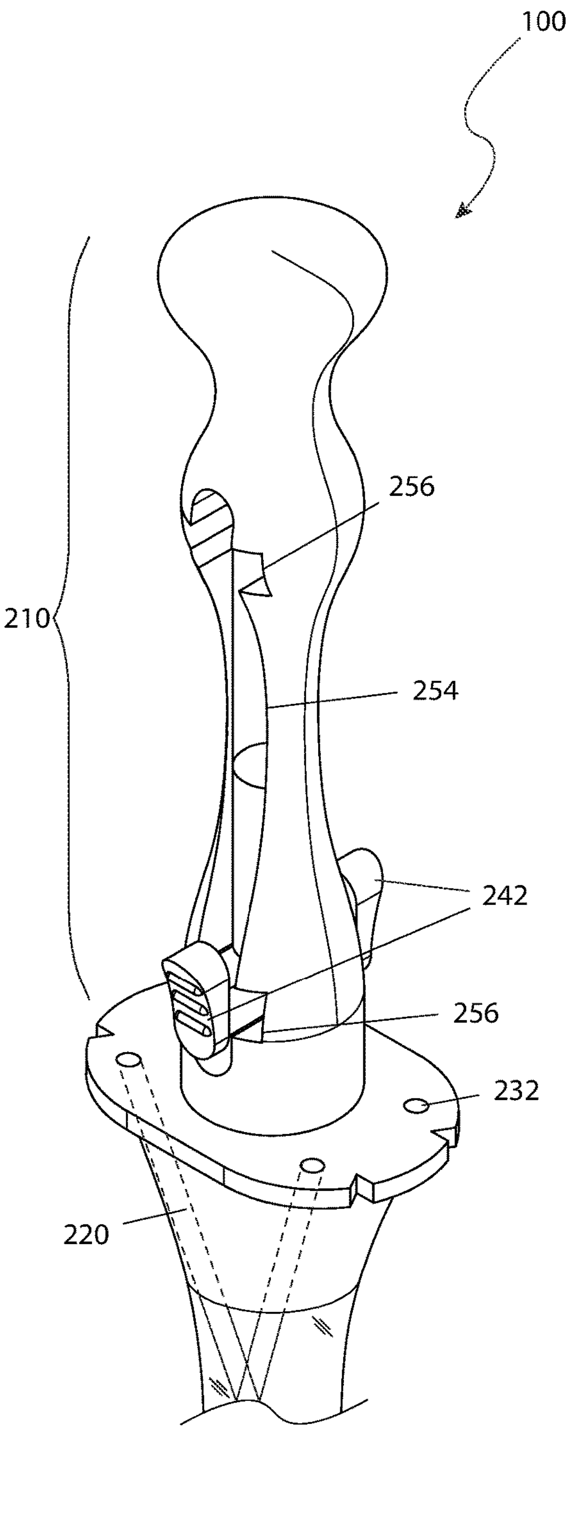
FIG. 17*b* is an isometric detail view of a fascia suturing system 100, according to an embodiment of the present invention, illustrating the proximal end 210 of the suture delivery device.

An individual needle guide lumen 230 may comprise a needle guide opening 232 and a needle guide exit 234 as seen in FIGS. 2, 15, and 17*b*. The needle guide opening 232 may be located on the top of the stopper 220 as seen in FIG. 17*b*. The needle guide exit 234 may be located on the side of the delivery body 202 that is opposite the needle guide opening 232 at a point between the stopper 220 and the plurality of wings 250 as seen in FIG. 15. The individual needle guide lumen 230 may be oriented such that the needle 276 pushed through the individual needle guide lumen 230 will intersect with the wing aperture 252 on the same side as the needle guide exit 234 when the plurality of wings 250 and the plurality of shields 260 are deployed as seen in FIG. 15.

The proximal end 190 of the actuator rod 244 may be coupled to the mounting structure 224 and the distal end 192 of the actuator rod 244 may be coupled to the proximal end 190 of a pull rod 240 as seen in FIG. 1. The distal end 192 of the pull rod 240 may comprise a pair of pull rod handles 242. The pair of pull rod handles 242 may be located on opposing sides of the pull rod 240. The combination of the actuator rod 244 and the pull rod 240 may slide longitudinally within the actuator lumen 222. The actuator lumen 222 may be a longitudinally-oriented cavity within the delivery body 202 as seen in FIG. 1. Each pull rod handle 242 may have a pull rod handle groove 243 on the proximal part thereof to be used as an anchor point to the two (2) sutures 900, 902 when mounted for stability thereof as seen in FIG. 4.

The pair of pull rod handles 242 may be accessible via a pair of pull rod apertures 254 located on the proximal portion 210 of the delivery body 202 as seen in FIG. 2. The pair of pull rod apertures 254 may be slots located on opposing sides of the proximal portion 210 of the delivery body 202 as seen in FIG. 3. The pair of pull rod apertures 254 may comprise a pair of locking notches 256 located at the proximal ends 190 of the pair of pull rod apertures 254 and at the distal ends 192 of the pair of pull rod apertures 254 in the proximal section 210 as seen in FIGS. 2 and 3. The pair of locking notches 256 may be operable to retain the pair of pull rod handles 242 in order to prevent longitudinal movement of the pull rod 240. The pair of pull rod handles 242 may comprise longitudinally-oriented pull rod handle groove 243 for securing the ends of the two (2) sutures 900, 902 as seen in FIG. 4.

The plurality of wings 250 and the plurality of shields 260 may be located adjacent to the delivery body 202 during insertion into the laparoscopic or robotic skin incision 912 and may be deployed by reconfiguring the plurality of wings 250 and the plurality of shields 260 into two (2) triangle structures located on opposing sides of the distal portion 212 of the delivery body 202.

The distal end 192 of an individual wing 250 may be pivotably coupled to the delivery body 202 and the proximal end 190 of the individual wing 250 may be pivotably coupled to the distal end 192 of an individual shield 260. The distal end 192 of the individual shield 260 may be pivotably coupled to the mounting structure 224. With the pair of pull rod handles 242 pushed down to the proximal end 190 of the pair of pull rod apertures 254, the mounting structure 224 may be extended downwards and may pull the proximal end 190 of the individual shield 260 downward as seen in FIG. 2. This may pull the individual shield 260 and the individual wing 250 into a linear orientation that places both the individual shield 260 and the individual wing 250 adjacent to the delivery body 202 for insertion into the laparoscopic or robotic skin incision 912 and into the fascia opening 920 and peritoneum layer 922. Pulling the pair of pull rod handles 242 up to the top of the pair of pull rod apertures 254 may move the mounting structure 224 upwards causing the individual shield 260 and the individual wing 250 to pivot such that an individual triangle structure is formed against the peritoneum layer 922 of the inner abdominal wall as seen in FIGS. 3 and 7.

The individual triangle structure may be a right triangle. The individual shield 260 may form the hypotenuse of the right triangle and the individual wing 250 may form the first leg of the right triangle. The second leg of the right triangle may be a line from the distal end 192 of the individual wing 250 to the mounting structure 224. The second leg may be considered to be parallel to the delivery body 202 as seen in FIG. 3.

When deployed, the individual wing 250 may be extended perpendicularly away from the delivery body 202. The individual wing 250, the individual shield 260, and the delivery body 202 may define a suture retrieval space 262 as seen in FIG. 1 within the individual triangle structure and the two (2) sutures 900, 902 may pass through the suture retrieval space 262 as seen in FIG. 8. The individual wing 250 may comprise the wing aperture 252 that the needle 276 of the suture retriever 270 may pass through in order to grasp one (1) of the two (2) sutures 900, 902 from within the suture retrieval space 262 as seen in FIG. 8. The size and shape of the wing aperture 252 may assure that the needle 276 passing through either of the plurality of needle guide lumens 230 that are pointed at the individual wing 250 may reach the two (2) sutures 900, 902 within the suture retrieval space 262 with no mechanical interference from the individual wing 250.

Figure 14:
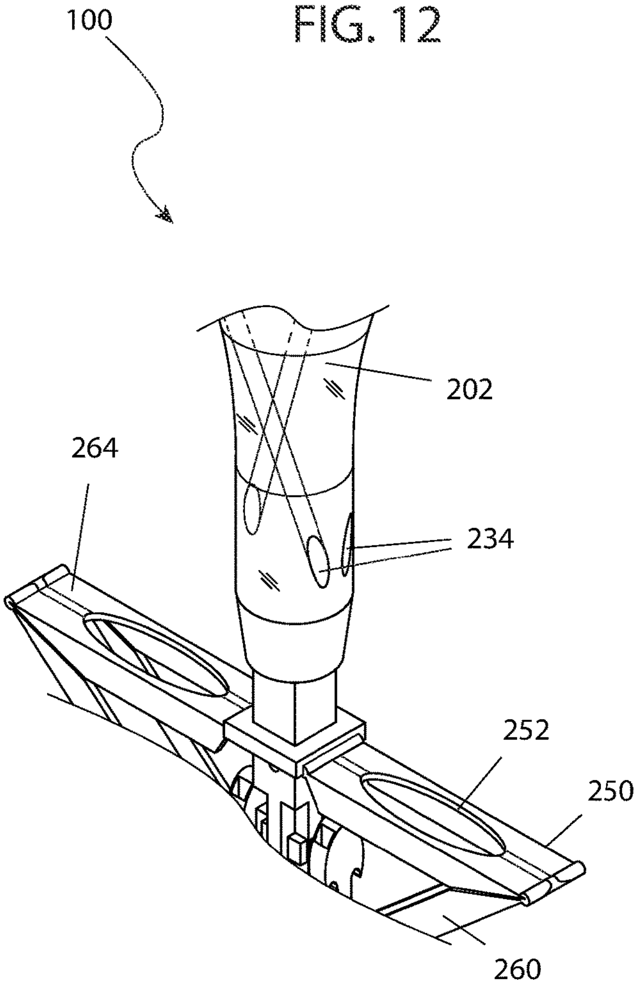
FIG. 14 is a detail view of a fascia suturing system 100, according to an embodiment of the present invention, illustrating wing apertures 252 and widened suture gaps 264 on the plurality of wings 250.

The individual wing 250 may comprise a suture gap 264 oriented longitudinally on the individual wing 250 with a wider opening at the edge such that the two (2) sutures 900, 902 may pass through the individual wing 250 to be retained by the suture guide 208 as seen in FIGS. 12 and 14. In comparison, the individual shield 260 has no such gap. The two (2) sutures 900, 902 rest upon the outside surface of the individual shield, pass through the suture gap 264 on the individual wing 250, and are retained by the suture guide 208. This assure that when the plurality of wings 250 and the plurality of shields 260 are deployed that the two (2) sutures 900, 902 will extend upwards from the mounting structure 224 at an oblique angle on the outside of the individual shield 260, will turn towards the delivery body 202 at the junction of the individual shield and the individual wing 250, will pass through the suture retrieval space 262 to the suture guide 208, and will then continue upwards along the side of the delivery body 202 to the stopper 220 as seen in FIG. 15.

The individual shield may assure that the needle 276 does not contact or damage the internal organs as seen in FIG. 8. Once the plurality of wings 250 and the plurality of shields 260 have been deployed, the medical professional may pull up gently on the distal end 192 of the suture delivery device 200 until the plurality of wings 250 contact the subcutaneous layers 916 as an indication that the suture delivery device 200 is at a proper depth below the fascia opening 920 and the peritoneum layer 922 as seen in FIG. 7.

Figure 9:
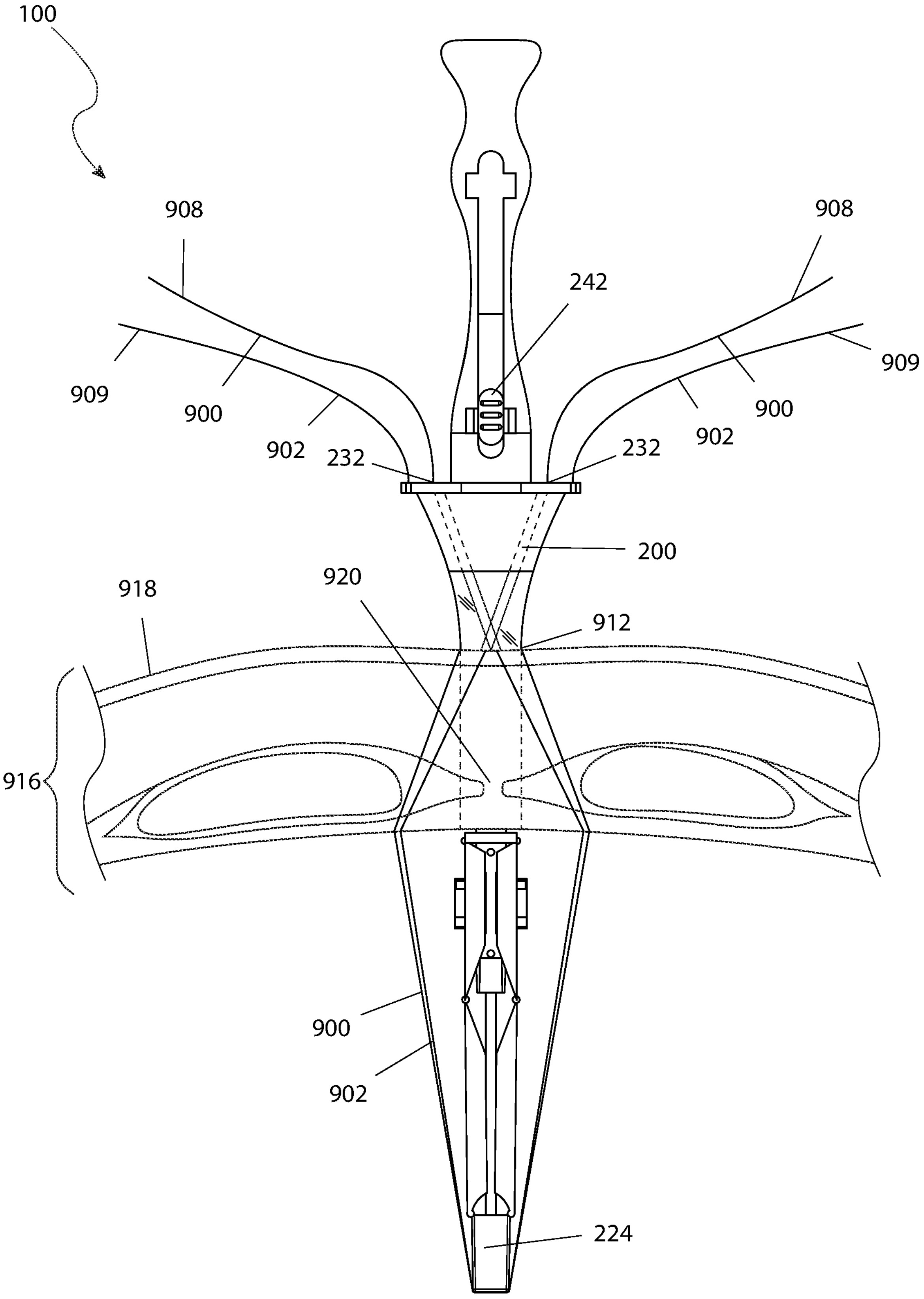
FIG. 9 is an in-use view of a fascia suturing system 100, according to an embodiment of the present invention, illustrating the first suture free ends 908 and the second suture free ends 909 being retrieved through the needle guide openings 232 and the suture delivery device collapsed by pressing the pair of pull rod handles 242 down.
Figure 10A:
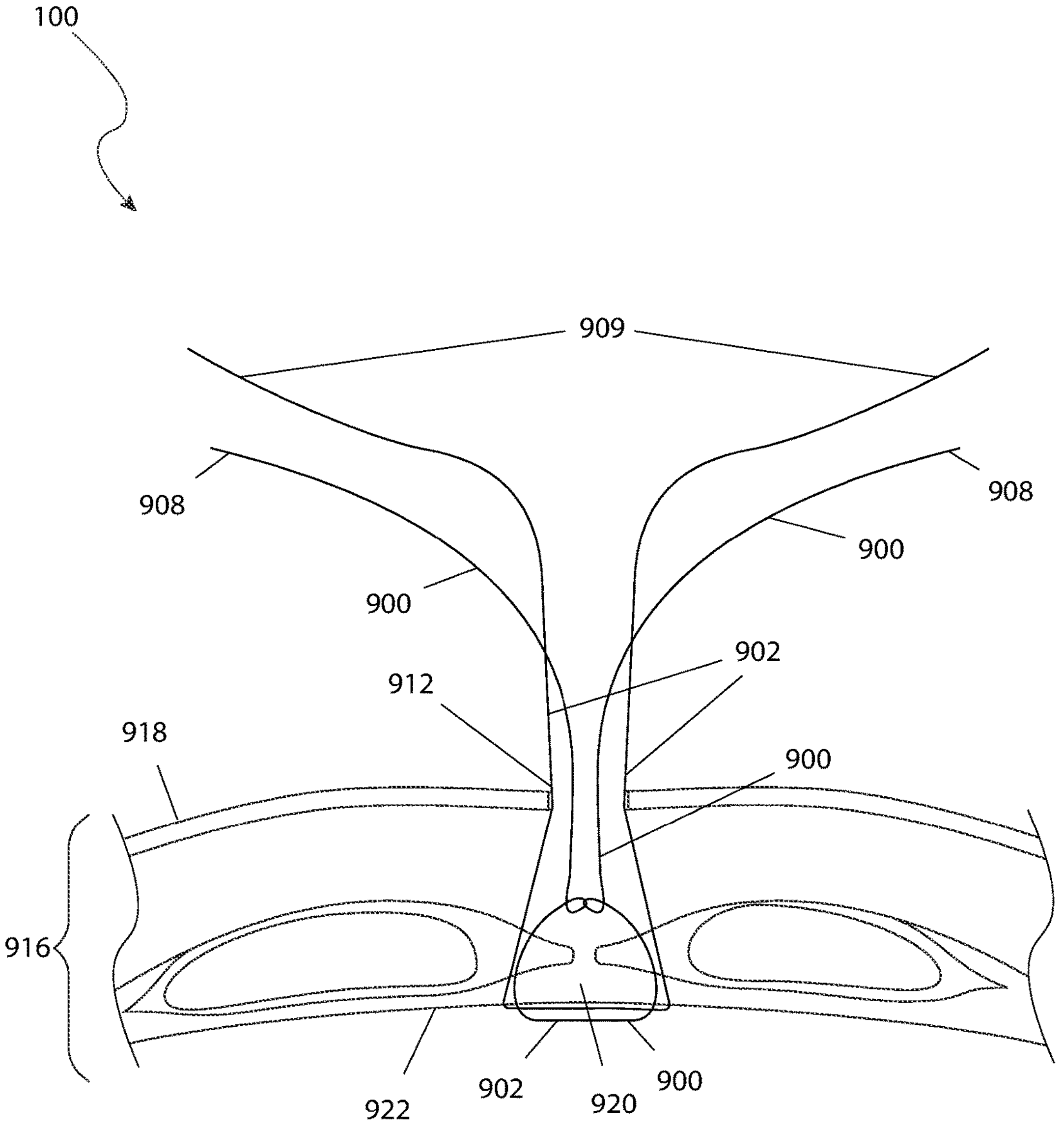
FIG. 10*a* is an in-use view of a fascia suturing system 100, according to an embodiment of the present invention, illustrating the suture delivery device withdrawn from the fascia incision 620 and the second suture free ends 909 ready to be pulled tight and tied to close the fascia incision 620, while the first suture 900 has already been tightened down approximating the muscles completely closing the fascia incision 620.
Figure 10B:
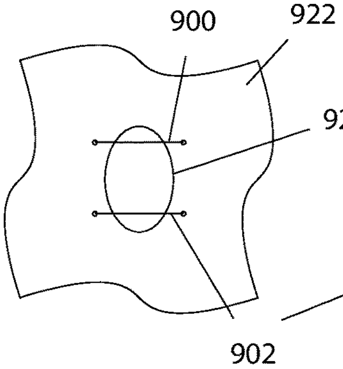
FIG. 10*b* is an alternate illustration of a straight closure with the first and second sutures 900, 902 of the fascia incision 920 and peritoneum layer 922.
Figure 10C:
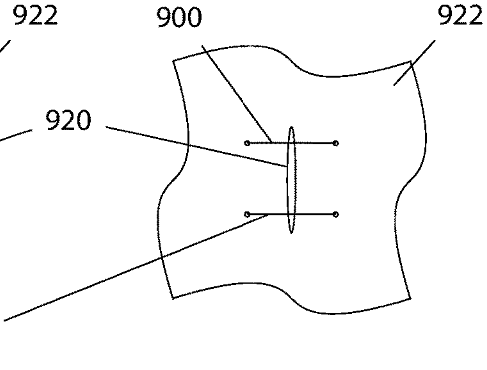
FIG. 10*c* is another alternate illustration of a straight closure with the first and second sutures 900, 902 of the fascia incision 920 and peritoneum layer 922.
Figure 10D:
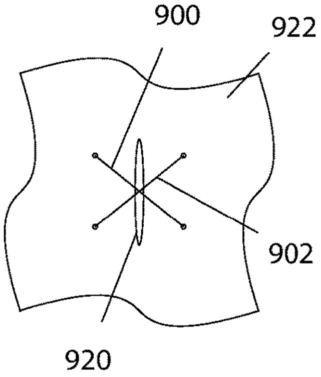
FIG. 10*d* is an alternate illustration of a crossed closure with the first and second sutures 900, 902 of the fascia incision 920 and peritoneum layer 922.

The suture retriever 270 may be adapted to pierce the subcutaneous layers 916, included inside this layer the muscle 924, fascia opening 920 and peritoneum layer 922, guided by the suture delivery device 200 and to grasp one (1) of the individual sutures 900, 902 that are traversing the suture retrieval space 262. The suture retriever 270 may then extract a first suture free end 908 through the site where the suture retriever 270 pierced the subcutaneous layers 916. As the suture retriever 270 pulls on the individual suture, the first suture free end 908 may be pulled down along the side of the suture delivery device 200 and up through the site where the suture retriever 270 pierced the subcutaneous layers 916 until the first suture free end 908 is retrieved as seen in FIG. 9.

As a non-limiting example, the suture retriever 270 may be used four (4) times to grasp and extract both the first suture free end 908 and second suture free end 909. Specifically, the suture retriever 270 may be used twice from opposing sides in front of the wing plane and twice from opposing sides behind the wing plane.

The suture retriever 270 may comprise a retriever handle 274, the needle 276, and a push button 286 as seen in FIG. 18*a*. The retriever handle 274 may be adapted to be grasped by the medical professional in order to extract either a first suture free end 908 or a second suture free end 909. The retriever handle 274 may comprise a retriever lumen 294 and a finger hold 292. The retriever lumen 294 may be an internal longitudinally-oriented cavity that the push button 286 may slide within. The finger hold 292 may be an armature located at the proximal end of the retriever handle 274 that may be adapted to be held by fingers while actuating the push button 286.

The push button 286 may be adapted for the medical professional to press in order to actuate a pair of pinchers 280 that may grasp the individual suture. The push button 286 may expose a flattened surface at the proximal end of the suture retriever 270 for pressing with a finger. A portion of the push button 286 may slide up and down within the retriever lumen 294. One (1) or more retriever springs 278 within the retriever lumen 294 may bias the push button 286 to rise in the absence of an external downward force.

The push button 286 may comprise an automatic stopper 288. The automatic stopper 288 may be a tab projecting laterally from the side of the push button 286 that may engage a locking window 290 on the retriever handle 274. The locking window 290 and the automatic stopper 288 may be positioned such that the automatic stopper 288 engages the locking window 290 when the push button 286 is fully depressed. Once engaged, the automatic stopper 288 may prevent the push button 286 from moving in a proximal direction until a force is applied latterly to the automatic stopper 288 to disengage the automatic stopper 288 from the locking window 290. In some embodiments, one (1) or more retriever springs 278 may bias the push button 286 to push the automatic stopper 288 into the locking window 290 when the automatic stopper 288 and the locking window 290 are aligned.

The needle 276 may be a hollow cylindrical tube that may be coupled to the distal end 192 of the retriever handle 274. The needle 276 may be adapted to pierce the subcutaneous layers 916 as the suture retriever 270 is pushed through one (1) of the plurality of needle guide lumens 230 on the suture delivery device 200. The length of the needle 276 may assure that the distal end 192 of the needle 276 is able to reach through the suture retrieval space 262 created by deployment of the plurality of wings 250 and the plurality of shields 260 of the suture delivery device 200 to contact the individual shield 260.

The distal end 192 of the pair of pinchers 280 may be coupled to the proximal end 190 of the push button 286. The proximal end 190 of the pair of pinchers 280 may be accessible at the proximal end 190 of the needle 276. The pair of pinchers 280 may be retracted into the proximal end 190 of the needle 276 while the needle 276 is pushed through the subcutaneous layers 916. The pair of pinchers 280 may be deployed by pressing the push button 286 to extend the pair of pinchers 280 out of the proximal end 190 of the needle 276 when the proximal end 190 of the needle 276 is positioned within the suture retrieval space 262 of the suture delivery device 200.

As a non-limiting example, the pair of pinchers 280 as seen in FIG. 19 may comprise a straight armature 282 and a hooked armature 284 that may separate when extended from the distal end 192 of the needle 276. The straight armature 282 and the hooked armature 284, once separated, may straddle the individual suture and may be retracted to capture the individual suture between the straight armature 282 and the hooked armature 284as seen in FIG. 19. The suture retriever 270 may then be withdrawn from the suture delivery device 200 to retrieve the free end 908 of the individual suture.

After the first suture free ends 908 and second suture free end 909 are retrieved, the plurality of wings 250 and the plurality of shields 260 may be collapsed by moving the pair of pull rod handles 242 down and the suture delivery device 200 may be withdrawn from the laparoscopic or robotic skin incision 912 as seen in FIG. 9. The closing procedure may be completed by tying surgical knots to retain the two (2) sutures 900, 902 as seen in FIG. 10.

In use, two (2) sutures 900, 902 may be affixed to the suture delivery device 200 in preparation for a closing procedure. As a non-limiting example, a first suture 900 may be affixed to the suture delivery device 200 in front of the wing plane and a second suture 902 may be affixed to the suture delivery device 200 behind the wing plane. For each of the two (2) sutures 900, 902, one (1) end of an individual suture 900, 902 may be placed into one (1) of the pair of stopper notches 206 on a first side of the stopper 220, the individual suture 900, 902 may be wrapped around the mounting structure 224 at the proximal end 190 of the suture delivery device 200, and the other end of the individual suture 900, 902 may be placed into one (1) of the pair of stopper notches 206 on a second side of the stopper 220. The individual suture 900, 902 may then be repositioned to pass behind the suture guide 208 on each side of the suture delivery device 200.

The suture delivery device 200 may be inserted through the laparoscopic or robotic skin incision 912 and the plurality of wings 250 and the plurality of shields 260 may be deployed by pressing down on the pair of pull rod handles 242. With the plurality of wings 250 and the plurality of shields 260 deployed, the medical professional may pull up gently until the plurality of wings 250 contact the peritoneum layers 922 to position the suture delivery device 200 at a correct depth as seen in FIG. 7.

The medical professional may then retrieve the first suture free ends 908 and second suture free end 909. For each first suture free end 908 and second suture free end 909, the medical professional may insert the suture retriever 270 through one (1) of the plurality of needle guide lumens 230 into the subcutaneous layers 916, thereby piercing the subcutaneous layers 916 in the process. The medical professional may press down on the push button 286 of the suture retriever 270 to extend and open the pair of pinchers 280. The automatic stopper 288 may engage the locking window 290 to hold the pair of pinchers 280 open. The pair of pinchers 280 may straddle the individual suture and the medical professional may press the automatic stopper 288 to disengage the automatic stopper 288 from the locking window 290, thus closing the pair of pinchers 280 on the individual suture. The suture retriever 270 may be withdrawn from the suture delivery device 200, pulling the free end 908 of the individual suture with it.

After the free ends 908 of the two (2) sutures are retrieved, the plurality of wings 250 and the plurality of shields 260 may be collapsed by moving the pair of pull rod handles 242 down and the suture delivery device 200 may be withdrawn from the laparoscopic incision 912. The closing procedure may be completed by tying surgical knots to retain the two (2) sutures 900, 902, thereby closing the fascia opening 920 in a safe way. Following this, the laparoscopic or robotic skin incision 912 is closed in the standard manner by approximating the ends using staples or simple absorbable sutures.

The benefits of this fascia suturing system 100 to the patients is multifactorial. It will provide a safe and secure closure for a fascia opening 920 to decrease the risk of future incisional hernia. It will decrease the operative time by providing the placement of two (2) sutures 900, 902 at the same time. By decreasing the operative time, it will decrease the risk of the anesthesia exposure to the patient which will decrease any pulmonary and cardiac complications. It also can control bleeding from edges of laparoscopic or robotic skin incisions 912 by proper positioning and orientation of the sutures 900, 902.

The exact specifications, materials used, distances of the different portions of the delivery body 202, and method of use of the fascia suturing system 100 may vary upon manufacturing. The foregoing descriptions of specific embodiments of the present device have been presented for purposes of illustration and description. They are not intended to be exhaustive or to limit the device to the precise forms disclosed, and obviously many modifications and variations are possible in light of the above teaching. The embodiments were chosen and described in order to best explain the principles of the device and its practical application, to thereby enable others skilled in the art to best utilize the device and various embodiments with various modifications as are suited to the particular use contemplated.

What is claimed is:

1. A fascia suturing system, comprising:

a suture delivery device having a delivery body configured to facilitate insertion through a laparoscopic or robotic skin incision into an abdominal cavity of a patient, the suture delivery device equipped with a plurality of deployable wings and a plurality of deployable shields for positioning at least two sutures beneath a fascia opening and a peritoneum layer, each suture having first and second free ends; and a suture retention and routing system carried by the delivery body, the suture retention and routing system comprising:

a pair of suture positioning grooves running longitudinally along opposing sides of the delivery body from a stopper located on the delivery body to a suture guide on each side of the delivery body, said suture positioning grooves continuing along an outer surface of each of the plurality of deployable shields to guide and retain the at least two sutures along a defined suture path;

the suture guide on each side of the delivery body, each suture guide comprising a pair of suture guide notches on a bottom surface thereof configured to retain the at least two sutures against opposing sides of the delivery body during deployment of the plurality of deployable wings and the plurality of deployable shields, wherein each suture guide is positioned behind a respective one of the plurality of deployable wings when said wing is folded flat against the delivery body;

each wing of the plurality of deployable wings comprising a wing aperture and a suture gap, wherein the wing aperture is sized and shaped such that a needle of a suture retriever passing through any needle guide lumen directed at that wing reaches the at least two sutures within a suture retrieval space defined between the wing and an adjacent shield without mechanical interference from the wing, and wherein the suture gap is oriented longitudinally along the wing with a wider opening at an outer edge of the wing configured to allow a respective one of the at least two sutures to pass laterally through the wing to the suture guide positioned behind the wing, the plurality of deployable shields being free of any suture gap such that the at least two sutures rest upon the outer surface of each shield and turn through the suture gap of the adjacent wing into the suture retrieval space; and a mounting structure at a proximal end of the delivery body serving as a pivot point for a proximal end of each of the plurality of deployable shields, the mounting structure comprising a plurality of slots configured to guide the at least two sutures around the proximal end of the delivery body, wherein the plurality of slots comprises a pair of straight-across slots configured to align the at least two sutures in a parallel orientation relative to one another, and a pair of crossing slots configured to align the at least two sutures in a crossing orientation relative to one another, thereby enabling a user to selectively configure the at least two sutures as either parallel or crossing prior to insertion.

2. The system of claim 1, wherein the delivery body further comprises a plurality of needle guide lumens, and wherein:

each needle guide lumen comprises a needle guide opening located on a top surface of the stopper and a needle guide exit located on a side of the delivery body opposite the needle guide opening at a point between the stopper and the plurality of deployable wings, each needle guide lumen oriented such that the needle pushed therethrough intersects the wing aperture of a respective wing on the same side as the needle guide exit when the plurality of deployable wings and the plurality of deployable shields are in a deployed position;

front needle guide lumens of the plurality of needle guide lumens, located in front of a wing plane defined as an imaginary plane passing through a central longitudinal axis of the delivery body and through the center of the plurality of deployable wings, are each oriented at opposing oblique angles with respect to the central longitudinal axis; and rear needle guide lumens of the plurality of needle guide lumens, located behind the wing plane, are mirror images of the front needle guide lumens, such that the plurality of needle guide lumens collectively enable retrieval of both the first and second suture free ends from both in front of and behind the wing plane in a single insertion procedure.

3. The system of claim 1, further comprising a suture retriever configured to interact with the suture delivery device for fascia closure, the suture retriever comprising:

a retriever handle comprising a retriever lumen and a finger hold armature located at a proximal end of the retriever handle, the finger hold armature adapted to be held by fingers of a medical professional while a push button is actuated;

a hollow cylindrical needle coupled to a distal end of the retriever handle and adapted to pierce subcutaneous layers as the suture retriever is inserted through one of the plurality of needle guide lumens, the hollow cylindrical needle having a length sufficient for a distal end thereof to reach through the suture retrieval space to contact a respective one of the plurality of deployable shields;

a pair of pinchers comprising a straight armature and a hooked armature retractably housed within the needle, wherein upon extension from the distal end of the needle the straight armature and the hooked armature separate from one another to straddle a respective one of the at least two sutures, and upon retraction into a needle capture said suture therebetween for retrieval;

the push button slidably disposed within the retriever lumen and operably coupled to the pair of pinchers, wherein one or more retriever springs within the retriever lumen bias the push button to return to an undepressed position in the absence of an external downward force; and an automatic stopper comprising a tab projecting laterally from a side of the push button configured to engage a locking window on the retriever handle when the push button is fully depressed, the automatic stopper preventing the push button from returning to the undepressed position until a lateral force is applied to the automatic stopper to disengage it from the locking window, thereby retaining the pair of pinchers in an open straddling position to facilitate suture capture.

* * * * *